United States Patent [19]

Patel et al.

[11] Patent Number: 5,393,663

[45] Date of Patent: Feb. 28, 1995

[54] STEREOSELECTIVE PREPARATION OF HALOPHENYL ALCOHOLS FROM KETONES

[75] Inventors: Ramesh N. Patel, Bridgewater; Mark Liu, Edison, both of N.J.; Amit Banerjee, Newtown, Pa.; Laszlo J. Szarka, East Brunswick, N.J.

[73] Assignee: E. R. Squibb & Sons, Inc., Princeton, N.J.

[21] Appl. No.: 46,884

[22] Filed: Apr. 14, 1993

Related U.S. Application Data

[63] Continuation of Ser. No. 781,628, Oct. 23, 1991, abandoned.

[51] Int. Cl.$^6$ .................... C12P 17/16; C12P 7/22; C12P 17/12
[52] U.S. Cl. ..................... 435/118; 435/280; 435/156; 435/122
[58] Field of Search ................ 435/280, 156, 118, 122

[56] References Cited

U.S. PATENT DOCUMENTS

| | | | |
|---|---|---|---|
| 4,584,270 | 4/1986 | Sih | 435/128 |
| 4,601,987 | 7/1986 | Klibanov et al. | 435/280 |
| 4,605,655 | 8/1986 | Yevich et al. | 514/252 |
| 4,607,013 | 8/1986 | Mitsuda et al. | 435/280 |
| 4,800,162 | 1/1989 | Matson | 435/280 |
| 4,857,468 | 8/1989 | Kutsuki et al. | 435/280 |
| 4,868,344 | 9/1989 | Brown | 568/812 |
| 4,994,460 | 2/1991 | Dextraze et al. | 514/252 |

FOREIGN PATENT DOCUMENTS

| | | |
|---|---|---|
| 080827 | 6/1983 | European Pat. Off. . |
| 0198440 | 10/1986 | European Pat. Off. . |
| 266217 | 5/1988 | European Pat. Off. . |
| 328125 | 8/1989 | European Pat. Off. . |
| 350811 | 1/1990 | European Pat. Off. . |
| 385172 | 9/1990 | European Pat. Off. . |
| 2832602 | 2/1979 | Germany . |
| 2130207A | 5/1984 | United Kingdom . |
| 2155925A | 10/1985 | United Kingdom . |

OTHER PUBLICATIONS

Christen, M et al., J. Chem. Soc. Chem. Commun. 264–266 (1988).
Shen, G. et al., J. Chem. Soc. Chem Commun. 677–679 (1990).
Hummel, W., Appl. Microbiol. Biotechnol 34:15–19 (1990).
Ohta, H., Agrig. Biol. Chem. 51:2421–2427 (1987).
Imuta, M., J. Org. Chem. 45:3352–3355 (1980).
Jones J., Tetrahedron 42:3351–3403 (1986).
Nieduzak et al., Tetrahedron: Assymetry 2 (1991), 113 to 122.
Lauman et al., J. Chem. Soc. Chem. Commun. (1988), 598 to 600.
Sih et al., Developments in Industrial Microbiology, vol. 29, (1988) 221 to 229.
Feichter et al., Tetrahedron Letters 30 (5) 1989, 551–552.
Bianchi et al., J. Org. Chem. 53 (1988) 5531–5534.
Laumen et al., J. Chem. Soc., Chem. Commun. 3 (1989), 148–150.
Nakamura et al., Agric. Biol. Chem. 54 (6) (1990), 1569–1570.
Cambou et al., J. Am. Chem. Soc. 106 (1984) 2687 to 2692.
Hsu et al., Tet. Lett. 31 (1990), 6403 to 6406.
Babiak et al., J. Org. Chem. 55 (1990), 3377 to 3381.
Sih et al., Angew. Chem. 96 (1984), 556–564.

*Primary Examiner*—Douglas W. Robinson
*Assistant Examiner*—S. Saucier
*Attorney, Agent, or Firm*—Timothy J. Gaul

[57] ABSTRACT

A process is described for selectively preparing a compound of the formula

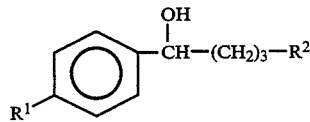

wherein:
$R^1$ is halogen;

(Abstract continued on next page.)

$R^2$ is halogen, alkyl, cycloalkyl, aryl or
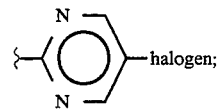
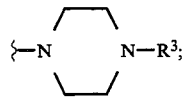
and
$R^3$ hydrogen, alkyl, cycloalkyl, aryl,
wherein the process comprises treating the associated ketone with an oxido-reductase or a microorganism comprising an oxidoreductase. Compounds prepared by this process are useful antipsychotic agents or useful intermediates therefor.
9 Claims, No Drawings

STEREOSELECTIVE PREPARATION OF HALOPHENYL ALCOHOLS FROM KETONES

This is a continuation of application Ser. No. 781,628, filed on Oct. 23, 1991, now abandoned.

FIELD OF INVENTION

This invention relates to preparation of antipsychotic agents and chemical intermediates, particularly BMY 14,802 and its intermediates.

BACKGROUND OF THE INVENTION

Antipsychotic agents are described in U.S. Pat. Nos. 4,605,655 and 4,994,460, issued Aug. 12, 1986 and Feb. 19, 1991, respectively. Of these agents, a compound identified as BMY 14,802 having the structure

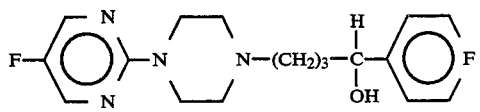

is preferred. The R(+) isomer of BMY 14,802 and the other compounds disclosed in these patents are believed to be more active, although S isomers are also useful antipsychotic agents. No enzymatic or microbial preparations of these compounds is known, and chemical stereoselective preparation is difficult. A need exists, therefore, for a stereoselective preparation of these compounds in high yield and high stereoisomeric purity.

BRIEF DESCRIPTION OF INVENTION

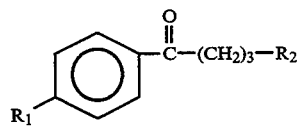

are selectively reduced to compounds of the formulas

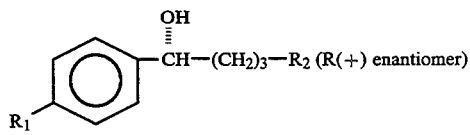

II

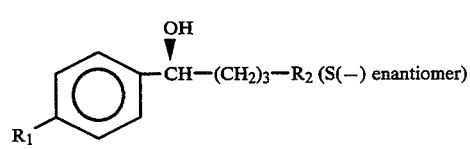

III by treatment with an oxido-reductase or a microorganism comprising an oxido-reductase, after which the product is recovered therefrom. In compounds I to III and throughout this specification, the symbols are defined as follows:
$R^1$ is halogen (fluorine preferred),
$R^2$ is halogen (chlorine preferred), alkyl, cycloalkyl, aryl or

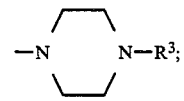

and
$R^3$ is hydrogen, alkyl, cycloalkyl, aryl or

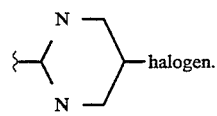

The following moieties are preferred for the process of this invention:
$R^1$ is fluorine; and
$R^2$

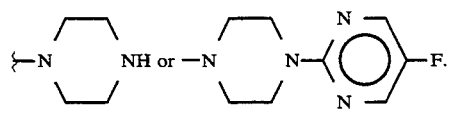

Compounds of formulas I, II and III are useful, inter alia, as antipsychotic agents or intermediates in the preparation thereof. See U.S. Pat. Nos. 4,605,655 and 4,994,460. Intermediates produced by the process of this invention may be used in procedures described in the cited patents to prepare useful antipsychotic agents.

The process has the advantage of producing a enantiospecific result. The process primarily yields the R(+) enantiomer rather than a mixture of preferred and unpreferred enantiomers. However, the process can also be used to selectively prepare the S(−) enantiomer. Additional advantages include a single step enantiospecific reduction compared with multi-step chemical synthesis. When the transformation is catalyzed at ambient temperature and pressure, one obtains high conversion and enantiomeric purity of the desired enantiomer.

DETAILED DESCRIPTION OF THE INVENTION

The following definitions apply throughout this specification, unless otherwise limited in specific instances. These definitions apply to the terms as used individually or as part of a larger group.

The term "alkyl" refers to straight and branched chain hydrocarbon groups having 1 to 10 carbon atoms.

The term "cycloalkyl" refers to groups having 3, 4, 5, 6 or 7 carbon atoms.

The term "aryl" refers to phenyl and substituted phenyl. Exemplary substituted phenyl groups are substituted with 1, 2 or 3 amino (—NH$_2$), alkylamino, dialkylamino, nitro, halogen, hydroxyl, trifluoromethyl, alkyl (of 1 to 4 carbon atoms), alkoxy (of 1 to 4 carbon atoms), alkanoyloxy, carbamoyl or carboxyl groups.

The term "halogen" refers to fluorine, chlorine, bromine and iodine.

"Transformation" as used herein refers to conversion of compound I to compound II or compound III.

"Fermentation" as used herein refers to growth of the microbial cells to be used in transformation.

The process of this invention can be carried out in a single stage or as a two-stage fermentation and transformation process.

In the single-stage process, the microorganisms are grown in an appropriate medium (e.g., media 1 to 6 hereinafter) containing carbon and nitrogen sources. After sufficient growth of microorganisms, a compound of formula I is added to the microbial cultures and transformation of compound I to either compound II or III may be continued until complete conversion is obtained.

In the two-stage process, microorganisms are grown in an appropriate medium by fermentation exhibiting the desired oxido-reductase activity in the first stage. Subsequently, cells are harvested by centrifugation. Microbial cell suspensions are prepared by suspending harvested cells in an appropriate buffered solution. Buffers such as tris-HCl phosphates, sodium acetate and the like may be used. Water can also be used to prepare suspensions of microbial cells to conduct the transformation process.

Compound I is mixed with the microbial cell suspensions, and the transformation of compound I to compound II or III is catalyzed by the microbial cell suspensions. The reaction may continue until nearly all of compound I is transformed.

Typical microorganisms suitable for this process include genera from bacteria, yeasts, and fungi. Preferred genera of microorganisms are: Achromobacter, Acinetobacter, Actinomyces, Alcaligenes, Arthrobacter, Azotobacter, Bacillus, Brevibacterium, Corynebacterium, Flavobacterium, Methylomonas, Mycobacterium, Nocardia, Pseudomonas, Rhodococcus, Streptomyces, Xanthomonas, Aspergillus, Candida, Fusarium, Geotrichum, Hansenula, Kloeckera, Penicillium, Pichia, Rhizopus, Rhodotorula, Saccharomyces, Trichoderma, Rhodopseudomonas, Pullularia, Mortierella, Torulopsis, Mucor, Beaubaria, paecilomyces, Lactobacilli, Trigonopsis, Acremonium, Gluconobacter, Streptomyces, Cunninghamella, and Cladosporium.

Preferred species are: *Arthrobacter simplex, Candida albicans, Candida boiidini, Cunninghamella echinalata, Geotrichum candidum, Hansenula anomala, Hansenula polymorpha, Lactobacillus kefir, Mortierella ramanniana, Mycobacterium vacca, Nocardia autotrophica, Nocardia globerula, Nocardia mediterranei, Nocardia petroleophila, Nocardia restricta, Nocardia salmonicolor, Pullularia pullulans, Rhodococcus equi, Rhodococcus fascians, Rhodococcus rhodochrous,* and *Saccharomyces cerevisiae.*

For preparation of the R-isomer product (compound II), compound I may be treated with microorganisms selected from the genera Arthrobacter, Candida, Hansenula, Mortierella, Mycobacterium, Nocardia, Pullularia, Rhodococcus, and Saccharomyces and the like, or with an oxido-reductase deriveable therefrom. The following species (or oxido-reductases deriveable therefrom) are preferred for preparation of compound II: *Arthrobacter simplex, Candida boidini, Hansenula anomala, Hansenula polymorpha, Mortierella ramanniana, Mycobacterium vacca, Nocardia globerula, Nocardia petroleophia, Pullularia pullulans, Rhodococcus rhodochrous, Saacharomyces cerevisiae* and the like. The following particular strains (or oxido-reductases deriveable therefrom) are most preferred for preparation of compound II: *Arthrobacter simplex* ATCC 6949, *Candida boidini* ATCC 32195, *Hansenula anomala* ATCC 20211 and 36903, *Hansenula polymorpha* ATCC 26012 and 86014, *Mortierella ramanniana* ATCC 38191, *Mycobacterium vacca* ATCC 29678, *Nocardia globerula* ATCC 21505, *Nocardia petroleophia* ATCC 15776, *Pullularia pullulans* ATCC 16623, *Rhodococcus* sp. ATCC 21243, *Rhodococcus rhodochrous* ATCC 29675, and *Saccharomyces cerevisiae* ATCC 60731.

For the preparation of compound III, the species and strains listed in Table 2 and oxido-reductases deriveable therefrom are preferred.

Microorganisms can be used in free state as wet cells, freeze-dried cells or heat-dried cells. Immobilized cells on support by physical adsorption or entrapment can also be used for this process. Microbially derived oxido-reductases may be used in free state or immobilized on support.

Appropriate media for growing microorganisms for this process typically include necessary carbon sources, nitrogen sources, and trace elements. Inducers may also be added. "Inducer" as used herein refers to any compounds having keto groups, such that the desired oxido-reductase is produced within the microbial cell. Compound I may be added as an inducer during growth of the microorganism.

Carbon sources include sugars such as maltose, lactose, glucose, fructose, glycerol, sorbitol, sucrose, starch, mannitol, propylene glycol, and the like; organic acids such as sodium acetate, sodium citrate, and the like; amino acids such as sodium glutamate and the like; alcohols such as ethanol, propanol, and the like.

Nitrogen sources include N-Z amine A, corn steep liquor, soy bean meal, beef extracts, yeast extracts, molasses, baker's yeast, tryptone, nutrisoy, peptone, yeastamin, sodium nitrate, ammonium sulfate, and the like.

Trace elements include phosphates and magnesium, manganese, calcium, cobalt, nickel, iron, sodium, and potassium salts.

It is within the scope of this invention that appropriate media may include more than one carbon or nitrogen source and may include a mixture of several.

Typical preferred media are as follows:

| Medium 1: | Amount |
| --- | --- |
| Glucose | 40 g |
| Yeast Extract | 3 g |
| (NH$_4$)$_2$HPO$_4$ | 13 g |
| MgSO$_4$.7 H$_2$O | 800 mg |
| ZnSO$_4$.7 H$_2$O | 60 mg |
| FeSO$_4$.7 H$_2$O | 90 mg |
| CuSO$_4$.5 H$_2$O | 5 mg |
| MnSO$_4$.4 H$_2$O | 10 mg |
| NaCl | 100 mg |
| H$_2$O | 1 L pH 7.2 |

| Medium 2: | Amount |
| --- | --- |
| Malt Extract | 1% |
| Yeast Extract | 1% |
| Peptone | 1% |
| Glucose | 2% |
|  | pH 7.0 |

| Medium 3: | Amount |
| --- | --- |
| Glucose | 2% |
| Propylene Glycol | 1.5% |
| Yeast Extract | 1% |
| Peptone | 0.3% |
|  | pH 6.5 |

| Medium 4: | Amount |
| --- | --- |
| Molasses | 2.5% |
| Neopeptone | 0.5% |
| Peptone | 0.5% |
| Tryptone | 0.5% |
| Beef Extract | 0.3% |
| KH$_2$PO$_4$ | 0.3% |
| NaCl | 0.25% |
| Distilled Water | pH 6.0 |

Medium 5:

| -continued | | | |
|---|---|---|---|
| Bacto Proteose Peptone | 10 g | Ammonium Citrate | 2 g |
| Bacto Beef Extract | 10 g | Sodium Acetate | 5 g |
| Bacto Yeast Extract | 5 g | Magnesium Sulfate | 0.1 g |
| Dextrose | 20 g | Manganese Sulfate | 0.05 g |
| Sorbitan Monooleate Complex | 1 g | Disodium Phosphate | 2 g |
| Final pH 6.5 + 0.2 at 25° C. | | | |
| Medium 6: | | | |
| Glucose | | 20 g | |
| Corn steep solid | | 35 g | |
| Ammonium Sulfate | | 5.0 g | |
| Soybean Oil | | 5.0 g | |
| Calcium Carbonate | | 3.5 g | |
| pH 6.8 adjusted | | | |

The pH of the medium should be adjusted to about 6 to 8, preferably 6.5, before sterilization at 121° C. for 30 minutes and to about 6.5 to 7.5, preferably 6.9, after sterilization. The pH may be maintained between about 4.0 and 9.0, preferably between about 5.0 and 7.0, during fermentation and transformation.

The temperature of the reaction mixture should be maintained to ensure that there is sufficient energy available for the process. The temperature is a measure of the heat energy available for the transformation process. A suitable temperature range is about 15° C. to 60° C. A preferred temperature range is about 25° C. to 50° C.

The agitation and aeration of the reaction mixture affects the amount of oxygen available during the transformation process in shake-flask cultures or fermentor tanks during growth of microorganisms in a single-stage or two-stage process. The agitation range from 50 to 1000 RPM is preferable, but 50 to 500 RPM is most preferred. Aeration of about 0.1 to 10 volumes of air per volume of media per minute (i.e., 0.1 to 10 v/vt) is preferred. Aeration of about 5 volumes of air per volume of media per minute (i.e., 5 v/vt) is most preferred.

The reaction time for the transformation process is about 12 to 48 hours, preferably 4 to 24 hours, measured from the time of initially treating the substrate (compound I) with the microorganism to achieve complete transformation of compound I.

The following examples and preparations describe the manner and process of making and using the invention and are illustrative rather than limiting. These examples represent preferred embodiments, although other embodiments fall within the spirit and scope of the invention.

Example 1

The substrate for this process is 4-chloro-1-(4-fluorophenyl)-1-butanone. The desired product is R(+)-α-(3-chloropropyl)-4-fluorobenzenemethanol.

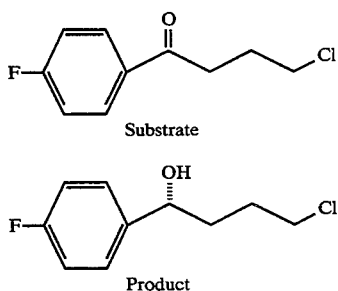

*Hansenula polymorpha* ATCC 86014 was maintained in a vial in liquid nitrogen. For routine development of inoculum, one vial was inoculated into 100 mL of medium 2 in a 500-mL flask and incubated at 28° C. and 280 RPM on a shaker for 48 hours. After growth of the microorganism, 10 mL of culture was inoculated into a 500-mL flask containing 100 mL of medium 2 and incubated at 28° C. and 250 RPM on a shaker.

Cells were harvested and suspended in 0.1M potassium phosphate buffer (pH 6.8). 10 mL of 15% w/v wet cell suspensions were prepared. Cell suspensions were supplemented with 20 mg of substrate and 750 mg of glucose and the transformation was conducted at 28° C., 280 RPM for 24 hours in a 125-mL flask. One volume of sample was taken and extracted with two volumes of ethyl acetate. The ethyl acetate layers were filtered through a 0.2 μM LID/X filter, collected and analyzed by gas chromatography (GC) for the identification of the substrate and product. The chromatographic conditions were as follows:

| | |
|---|---|
| Chromatograph: | Hewlett-Packard Model 5890 |
| Column: | HP.1, fused silica capillary column, 25 m, 0.32 mm I.D., 0.17 μm thickness |
| Injection Temperature: | 150° C. |
| Detector: | FID, 250° C. |
| Column Temperature: | 120° C.–150° C. (3° C./minute) |
| Injector: | Split mode |
| Carrier Gas: | He.Flow is controlled by head pressure |
| Hydrogen and Air Flow for FID: | Optimized |
| Split Flow: | 50 mL/minute (He) |
| Attenuation: | 20 |
| Chart Speed: | 1.0 cm/minute |
| Injection Volume: | 1 μL |
| Chromatographic Time: | 10 minutes |

The retention time for the substrate and product under above GC conditions are 5.0 and 5.8 minutes, respectively.

The optical purity of the product was determined by Chiral HPLC column, using UV (diode array) detector as follows:

| Hewlett Packard 1090L or suitable HPLC Backbond Chiralcel OB column | |
|---|---|
| Column Temperature: | 0° C. |
| Detector: | UV at 270 nm |
| Mobile Phase: | Hexane:Isopropanol:Ethanol 94:5:1 |
| Flow Rate: | 0.5 mL/minute |
| Retention Time: | R(+) enantiomer = 25.4 minutes S(−) enantiomer = 29.8 minutes |

Experimental results obtained by using various microorganisms grown in various media following the procedure of Example 1 are shown in Table 1. As can be seen from Table 1, all organisms converted the substrate to the desired product with 85–96% optical purity.

Some organisms selectively reduced the substrate to the S(−) stereoisomer, as shown in the
Table 2.

TABLE 1

Biotransformation of 4-chloro-1-(4-fluorophenyl)-1-butanone to R(+)-2-(3-chlorophenyl)-4-fluorobenzene-methanol

| Culture | Growth Medium | Reaction Time (hours) | Substrate (mg/ml) | Product (mg/ml) | Optical Purity (%) R(+)-product |
|---|---|---|---|---|---|
| *Hansenula polymorpha* ATCC 26012 | Medium 2 | 68 | 1.1 | 0.16 | 96 |
| *Hansenula polymorpha* ATCC 86014 | Medium 2 | 68 | 1.27 | 0.42 | 90 |
| *Rhodococcus sp.* ATCC 21243 | Medium 2 | 68 | 0.91 | 0.84 | 86 |
| *Nocardia globerula* ATCC 21505 | Medium 2 | 68 | 0.23 | 1.74 | 76 |
| *Nocardia petroleophila* ATCC 15776 | Medium 3 | 68 | 1.4 | 0.29 | 91 |
| *Arthrobacter simplex* ATCC 6949 | Medium 3 | 68 | 1.2 | 0.80 | 90 |
| *Rhodococcus rhodochrous* ATCC 29675 | Medium 3 | 68 | 1.04 | 0.50 | 86 |
| *Mycobacterium vacca* ATCC 29678 | Medium 2 | 68 | 0.42 | 1.40 | 85 |
| *Hansenula anomala* ATCC 20211 | Medium 3 | 44 | 0.73 | 0.51 | 82 |
| *Hansenula anomala* ATCC 36903 | Medium 3 | 68 | 0.61 | 1.14 | 90 |
| *Candida boidini* ATCC 32,195 | Medium 2 | 68 | 0.68 | 0.13 | 93 |
| *Saccharomyces cerevisiae* ATCC 60731 | Medium 3 | 68 | 0.68 | 0.85 | 92 |

TABLE 2

Biotransformation of 4-chloro-1-(4-fluorophenyl)-1-butanone to S(−)-2-(3-chlorophenyl)-4-fluorobenzene-methanol

| Culture | Growth Medium | Reaction Time (hours) | Substrate (mg/ml) | Product (mg/ml) | Optical Purity (%) S(−)-product |
|---|---|---|---|---|---|
| *Rhodococcus rhodochrous* ATCC 13808 | Medium 2 | 90 | 0.35 | 1.40 | 86 |
| *Pichia methanolica* ATCC 56508 | Medium 2 | 40 | 0.02 | 1.15 | 78 |
| *Pullularia pullulans* ATCC 16623 | Medium 3 | 68 | 0.26 | 1.08 | 89 |
| *Trigonopsis variables* ATCC 10679 | Medium 2 | 44 | 0.12 | 1.7 | 92 |
| *Cunninghamella echinalata* ATCC 26269 | Medium 6 | 40 | 0 | 1.5 | 96 |
| *Lactobacillus kefir* ATCC 35411 | Medium 5 | 16 | 0.02 | 1.60 | 96.5 |

EXAMPLE 2

The substrate for this process is 1-(4-fluorophenyl)-4-(1-piperazinyl)butan-1-one, 2-hydrochloride. The desired product is R(+)-1-(4-fluorophenyl)-4-(1-piperazinyl)butan-1-ol, 2-hydrochloride.

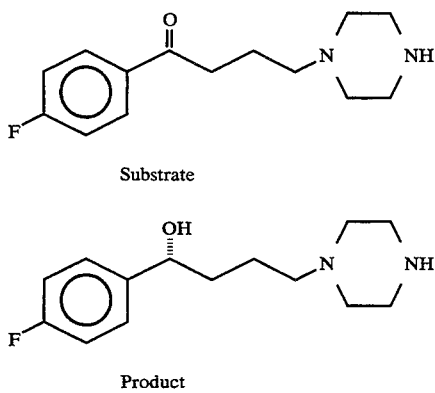

Substrate

Product

*Saccharomyces cerevisiae* ATCC 60731 was grown in medium 1 as described in Example 1. Cells were harvested and suspended in 0.1M potassium phosphate buffer (pH 6.8). The reaction was conducted in a 125-mL flask containing 10 mL of 20% cell suspensions in distilled water. Cerelose (750 mg) was added and incubated at 25° C., 280 RPM for at least 1 hour. Butanone (20 mg) was dissolved in 100 μL dimethyl formamide and substrate solution then added to the reactor and incubated at 25° C., 280 RPM. The reaction yield was determined by GC analysis of the reaction samples by methylene chloride/acetonitrile/isopropanol (60:35:5 v/v/v). GC assay was conducted under the following conditions:

Hewlett Packard 5890A gas chromatograph

Column: HP ultra-2 (25 m×0.32 mm×0.1 μm film thickness
Temperature: 190°–210° C., 2° C./min.
Run Time: 10 minutes
Detector: FID, 250° C.
Injector: 190° C., split mode
Injection Volume: 1 μL
Retention Time:
  Substrate: 3.8 minutes
  Product: 4.2 minutes The optical purity of product was determined by chiral HPLC column, using UV (diode array) detection. A Chiralcel OD column as ambient temperature was used. Mobile phase containing 1.5% n-butanol in hexane at flow rate of 0.5 ml/minute was used. The detection wavelength was 230 nm. The retention time for R(+)-enantiomer and S(−)-enantiomer were 10.54 minutes and 12.54 minutes respectively.

Using *Saccharomyces cerevisiae* ATCC 60731 culture for reduction reaction, a yield of 45% and an optical purity of 98% were obtained. Experimental results obtained by using microorganisms in appropriate growth medium and following the procedure in Example 2 are shown in Table 3.

EXAMPLE 3

The Substrate for this process is 1-(4-fluorophenyl)-4-[4-(5-fluoro-2-pyrimidinyl)-1-piperazinyl]-1-butanone.
The desired product is R(+)-1-(4-fluorophenyl-4-[4-(5-fluoro-2-pyrimidinyl)-1-piperazinyl]-1-butanol.

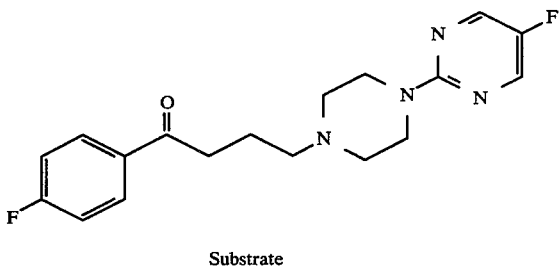

Substrate

Backbond chiralcel OD column
Column temperature: 20° C.
Mobile phase: Heptane:butanol:cyclohexanol, 97:2:1
Detector: UV at 270 mM
Flow Rate: 1 mL/minute
Retention Times:
  R(+) enantiomer: 25 minutes
  S(−) enantiomer: 31 minutes Experimental results obtained by using microorganisms in appropriate growth medium and following the procedure in Example 3 are shown in Table 4.

TABLE 3

Biotransformation of 1-(4-fluorophenyl)-4-(1-piperazinyl)butan-1-one, 2-hydrochloride to R(+)-1-(4-fluorophenyl)-4-(1-piperazinyl)butan-1-ol, 2-hydrochloride

| Culture | Growth Medium | Reaction Time (hours) | Substrate (mg/mL) | Product (mg/mL) | Optical Purity (%) R(+)-product |
|---|---|---|---|---|---|
| Nocardia globerula ATCC 21505 | Medium 1 | 96 | 1.5 | 0.5 | 95% |
| Saccharomyces cerevisiae ATCC 60731 | Medium 4 | 96 | 0.3 | 1.5 | 94% |
| Saccharomyces cerevisiae ATCC 60731 | Medium 6 | 96 | 0.4 | 1.2 | 90% |

TABLE 4

Biotransformation of racemic BMY 14802 to R-(+)- or S(−) BMY 14802

| Microorganism | Growth Medium | Reaction Time (hours) | Substrate (mg/ml) | Product (mg/ml) | Optical Purity (%) R(+)-product |
|---|---|---|---|---|---|
| Mortierella ramanniana ATCC 38191 | Medium 6 | 18 | 0.2 | 1.8 | 98.9 R-(+) |
| Pullularia pullulans ATCC 16623 | Medium 4 | 24 | 0.04 | 1.62 | 98.5 S(−) |
| Pullularia pullulans ATCC 16623 | Medium 2 | 96 | 0.47 | 1.22 | 98 S(−) |

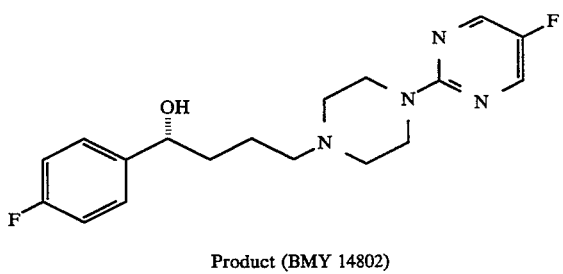

Product (BMY 14802)

Microorganisms were grown as described in Example 1. Cells were harvested and suspended in water.

The reaction was conducted in a 125-mL flask containing 10 mL of 15% cell suspensions in distilled water. Cerelose (750 mg) was added and incubated at 25° C., 280 RPM for at least 1 hour. Substrate (20 mg) was added to the reactor and incubated at 25° C., 280 RPM. The reaction yield was determined by GC analysis of the reaction samples by methylene chloride:acetonitrile:isopropanol mixture (60:35:5 v/v/v). Column: PIP ultra-2 capillary column (25 m×9.32 mm×0.17 μm film thickness)

Injector temperature 230° C.
Detector: FID,270° C.
Column temperature: 230° C.–270° C. (4° C./min.)
Carrier gas: Helium 40 ml/min. split flow
Injector: Split mode
The compounds were dissolved in the solvent mixture of methylene chloride:acetonitrile: isopropanol 60:35:5 (v/v/v).
Retention Times: Substrate: 5.2 minute
Product: 5.6 minutes The optical purity of product was determined by chiral HPLC column using UV (diode array) detector as follows:

Hewlett Packard 1090 L or suitable HPLC

EXAMPLE 4

The substrate for this procedure was 1-(4-fluorophenyl)-4-[4-(5-fluoro-2-pyrimidinyl)-1-piperazinyl]-1-butanone, and the desired product was the R isomer of BMY 14,802 (structures shown in Example 3). Cells of Mortierella ramanniana ATCC 38191 were grown in 250 L of medium 1 contained in a 380-L fermentor. Cells were grown as described below:

Inoculum Development

Inoculum development consisted of F1 and F2 stages. In the F1 stage, frozen vials of M.ramanniana (ATCC 38191) culture were inoculated into 100 mL of medium 6 contained in 500-mL flasks and incubated at 28° C., 280 RPM for 48–72 hours. In the F2 stage, 100 mL of F1 stage were inoculated into 1.5 L of medium 6 in a 4-L flask and incubated at 28° C., 180 RPM for 24 hours.

Fermentation

A fermentor containing 250 L of medium 6 was inoculated with 1.5 L of F2 stage inoculum. Fermentations were conducted for 48–68 hours at 150 RPM, 150 SLPM aeration, 28° C. Cells were harvested after 40 hours of growth and stored at −70° C. until further use.

Cells were suspended in 50 mL of 4-morpholineethanesulfonic acid (MES) buffer, pH 5.8, at 20% w/v (wet cells) concentration and disintegrated by sonication. Suspensions of sonicated cells were centrifuged at 5,000 RPM for 30 minutes and the supernatant solution was collected (cell extracts). Biotransformation of the substrate was conducted using cell extracts in the presence of NADPH (nicotinamide adenine dinucleotide phosphate, reduced) as cofactor. The reaction mixture contained 10 mL cell extracts, 20 mg of substrate, and 10 mg of NADPH. The reaction was conducted at 28° C., 100 RPM on a shaker. Substrate and product were analyzed as described in Example 3. Optical purity of the product was determined as described in Example 3.

Results of analysis after 72 hours of reaction time gave 1.2 mg/mL of the R(+) product in 99% optical purity.

EXAMPLE 5

The substrate and desired product were the same as in Example 4.

Cells of *Mortierella ramanniana* ATCC 38191 were grown in a 25-L fermentor containing 15 L of Medium 6 as described in Example 4. After 40 hours of growth, 30 grams of substrate and 1 kg of Cerelose were added to the fermentor, and bioreduction continued in a single-stage fermentation/biotransformation process. After 24 hours, the reduction was completed with 2 g/L of the desired product in 99% optical purity.

What is claimed is:

1. A process for selectively preparing an R- or S-isomer of a product of the formula

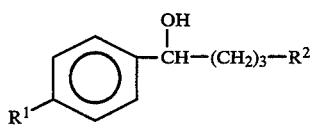

wherein:
R$^1$ is halogen;
R$^2$ is

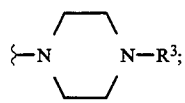

and
R$^3$ is hydrogen, alkyl, cycloalkyl, aryl, or

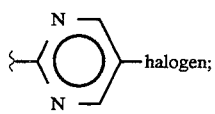

and wherein the process comprises:
(a) treating a substrate of the formula

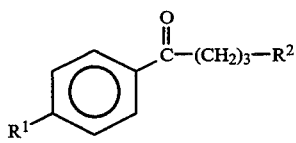

wherein R$^1$ and R$^2$ have the same meaning as above with a microorganism selected from a group consisting of:
*Hansenula polymorpha* ATCC 26012,
*Hansenula polymorpha* ATCC 86014,
*Rhodococcus sp.* ATCC 21243,
*Nocardia globerula* ATCC 21505,
*Nocardia petroleophila* ATCC 15776,
*Arthrobacter simplex* ATCC 6949,
*Rhodococcus rhodochrous* ATCC 29675,
*Mycobacterium vacca* ATCC 29678,
*Hansenula anomala* ATCC 36903,
*Candida boidini* ATCC 32,195,
*Saccharomyces cerevisiae* ATCC 60731,
*Rhodochococcus rhodochrous* ATCC 13808,
*Pichia methanolica* ATCC 56508,
*Pullalaria pullulans* ATCC 16623,
*Trigonopsis variables* ATCC 10679, and
*Cunninghamella echinalata* ATCC 26269,
or an oxidoreductase deriveable therefrom; and
(b) recovering the optically active product therefrom.

2. The process of claim 1, wherein R$^1$ is fluorine.

3. The process of claim 1, wherein R$^2$ is chlorine,

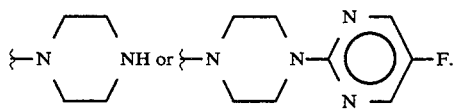

4. The process of claim 1, wherein the product is R(+)-1-(4-fluorophenyl-4-[4-(5-fluoro-2-pyrimidinyl)-1-piperazinyl]-1-butanol, the substrate is 1-(4-fluorophenyl)-4-[4-(5-fluoro-2-pyrimidinyl)-1-piperazinyl]-1-butanone, and the microorganism is *Mortierella ramanniana* ATCC 38191.

5. A process for selectively preparing an R-isomer of the formula

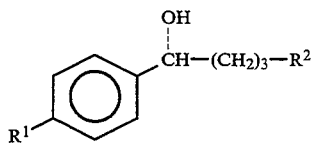

wherein:
R$^1$ is halogen;
R$^2$ is

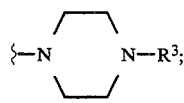

and
R$^3$ is hydrogen, alkyl, cycloalkyl, aryl, or

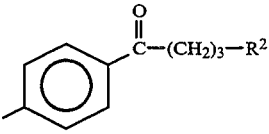

and wherein the process comprises:
(a) treating a substrate of the formula

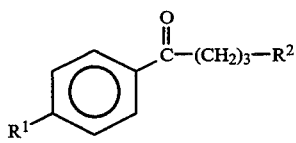

wherein R$^1$ and R$^2$ have the same meaning as above with a microorganism selected from a group consisting of:
*Arthrobacter simplex* ATCC 6949,
*Candida boidini* ATCC 32195,
*Hansenula anomala* 36903,
*Hansenula polymorpha* ATCC 26012 and 86014,
*Mycobacterium vacca* ATCC 29678,
*Nocardia globerula* ATCC 21505,

*Nocardia petroleophila* ATCC 15776,
*Pullularia pullulans* ATCC 16623,
*Rhodococcus sp.* ATCC 21243,
*Rhodococcus rhodochrous* ATCC 29675, and
*Saccharomyces cerevisiae* ATCC 60731 or an oxido-reductase deriveable therefrom; and
(b) recovering the optically active product therefrom.

6. The process of claim 5, wherein $R^1$ is fluorine.

7. The process of claim 5, wherein $R^2$ is chlorine,

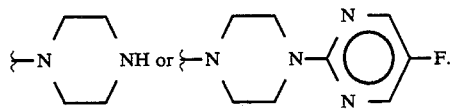

8. A process for selectively preparing an S-isomer product of the formula

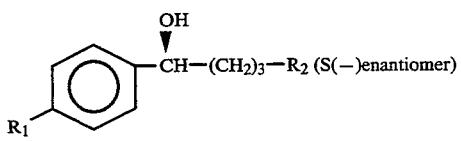

wherein:
$R^1$ is halogen,
$R^2$ is halogen, alkyl, cycloalkyl, aryl or

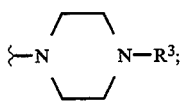

and
$R^3$ is hydrogen, alkyl, cycloalkyl, aryl, or

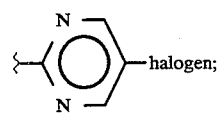

and wherein the process comprises:
(a) treating a substrate of the formula

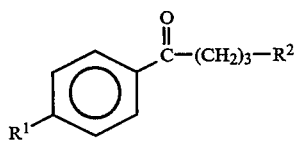

wherein $R^1$ and $R^2$ have the same meaning as above with a microorganism selected from:
*Rhodococcus rhodochrous* ATCC 13808,
*Pichia methanolica* ATCC 56508,
*Pullularia pullulans* ATCC 16623,
*Trigonopsis variables* ATCC 10679, and
*Cunninghamella echinalata* ATCC 26269, or an oxido-reductase deriveable therefrom; and
(b) recovering the optically active product therefrom.

9. A process for selectively preparing an R- or S-isomer of a product of the formula

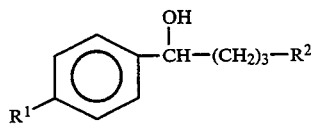

wherein:
$R^1$ is halogen;
$R^2$ is halogen, alkyl, cycloalkyl, aryl or

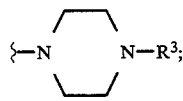

and
$R^3$ is hydrogen, alkyl, cycloalkyl, aryl, or

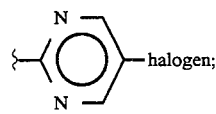

and wherein the process comprises:
(a) treating a substrate of the formula

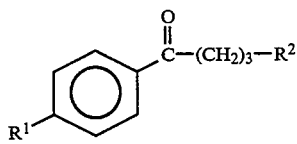

wherein $R^1$ and $R^2$ have the same meaning as above with a microorganism selected from a group consisting of:
*Hansenula polymorpha* ACTT 26012,
*Hansenula polymorpha* ACTT 86014,
*Rhodococcus sp.* ACTT 21243,
*Nocardia globerula* ACTT 21505,
*Nocardia petroleophila* ACTT 15776,
*Arthrobacter simplex* ACTT 6949,
*Rhodococcus rhodochrous* ACTT 29675,
*Mycobacterium vacca* ACTT 29678,
*Candida boidini* ACTT 32,195,
*Saccharomyces cerevisiae* ACTT 60731,
*Rhodochococcus rhodochrous* ACTT 13808,
*Pichia methanolica* ACTT 56508,
*Pullularia pullulans* ACTT 16623,
*Trigonopsis variables* ACTT 10679, and
*Cunninghamella echinalata* ACTT 26269, or an oxidoreductase deriveable therefrom; and
(b) recovering the optically active product therefrom.

* * * * *